(12) United States Patent
Hay et al.

(10) Patent No.: US 9,468,692 B2
(45) Date of Patent: Oct. 18, 2016

(54) LABELED MOLECULAR IMAGING AGENTS AND METHODS OF USE

(71) Applicant: GENERAL ELECTRIC COMPANY, Schenectady, NY (US)

(72) Inventors: Bruce Allan Hay, Niskayuna, NY (US); Jack Mathew Webster, Colonie, NY (US)

(73) Assignee: General Electric Company, Niskayuna, NY (US)

( * ) Notice: Subject to any disclaimer, the term of this patent is extended or adjusted under 35 U.S.C. 154(b) by 239 days.

(21) Appl. No.: 14/161,809

(22) Filed: Jan. 23, 2014

(65) Prior Publication Data

US 2015/0202332 A1    Jul. 23, 2015

(51) Int. Cl.
| | | |
|---|---|---|
| *A61K 51/00* | (2006.01) |
| *A61M 36/14* | (2006.01) |
| *A61K 51/04* | (2006.01) |
| *C07C 271/22* | (2006.01) |
| *C07C 311/19* | (2006.01) |
| *C07C 233/47* | (2006.01) |
| *C07C 233/51* | (2006.01) |
| *C07C 233/83* | (2006.01) |
| *C07C 235/52* | (2006.01) |
| *C07B 59/00* | (2006.01) |

(52) U.S. Cl.
CPC ......... *A61K 51/0406* (2013.01); *C07B 59/001* (2013.01); *C07C 233/47* (2013.01); *C07C 233/51* (2013.01); *C07C 233/83* (2013.01); *C07C 235/52* (2013.01); *C07C 271/22* (2013.01); *C07C 311/19* (2013.01)

(58) Field of Classification Search
CPC ............ A61K 51/0406; C07C 271/22; C07C 311/19; C07C 233/47; C07C 233/51; C07C 233/83; C07C 235/52; C07B 59/001
USPC ....................................................... 424/1.81
See application file for complete search history.

(56) References Cited

U.S. PATENT DOCUMENTS

| | | |
|---|---|---|
| 5,171,563 A | 12/1992 | Abrams et al. |
| 6,306,911 B1 | 10/2001 | Wachter et al. |
| 6,953,567 B2 | 10/2005 | Griffiths |
| 7,196,063 B1 | 3/2007 | Shirvan et al. |
| 7,211,240 B2 | 5/2007 | Arbogast et al. |
| 7,279,170 B2 | 10/2007 | Content et al. |
| 7,902,332 B2 | 3/2011 | De Jesus et al. |
| 7,906,103 B2 | 3/2011 | Graupner |
| 8,486,370 B2 | 7/2013 | Carpenter et al. |
| 2007/0014719 A1 | 1/2007 | Reading et al. |
| 2009/0022664 A1 | 1/2009 | Srinivasan et al. |
| 2010/0021379 A1 | 1/2010 | Lam et al. |
| 2010/0272641 A1 | 10/2010 | Webster et al. |
| 2010/0324008 A1 | 12/2010 | Low et al. |
| 2011/0165076 A1 | 7/2011 | Dinkelborg et al. |
| 2011/0250137 A1* | 10/2011 | Koglin et al. ............... 424/1.89 |

FOREIGN PATENT DOCUMENTS

| | | | |
|---|---|---|---|
| WO | 2006096207 A2 | 9/2006 |
| WO | WO 2010125068 A2 * | 11/2010 |
| WO | 2011057986 A1 | 5/2011 |
| WO | 2011061154 A1 | 5/2011 |
| WO | WO 2012150220 A1 * | 11/2012 |

OTHER PUBLICATIONS

Patani et al. Chem. Rev. 1996, 96, 3147-3176.*
He et al. J. Radioanal. Nucl. Chem. 2010, 286, 135-140.*
Banjac et al., "The Cystine/Cysteine Cycle: A Redox Cycle Regulating Susceptibility Versus Resistance to Cell Death", Oncogene, vol. 27, pp. 1618-1628, 2008.
Bassi et al., "Identification and Characterisation of Human xCT That Co-Expresses, With 4F2 Heavy Chain, the Amino Acid Transport Activity System xc", Pflugers Arch—Eur J Physiol, vol. 442, pp. 286-296, 2001.
Dai et al., "Chemoinformatics Analysis Identifies Cytotoxic Compounds Susceptible to Chemoresistance Mediated by Glutathione and Cystine/Glutamate Transport System xc", J. Med. Chem., vol. 50, pp. 1896-1906, 2007.
Gout et al., "Sulfasalazine, a Potent Suppressor of Lymphoma Growth by Inhibition of the xc Cystine Transporter: A New Action for an Old Drug", Leukemia, vol. 15, pp. 1633-1640, 2001.
Huang et al., "Cystine-Glutamate Transporter SLC7A11 in Cancer Chemosensitivity and Chemoresistance", Cancer, Res, vol. 65, No. 16, pp. 7446-7454, Aug. 15, 2005.
Kim et al., "Human Cystine/Glutamate Transporter: cDNA Cloning and Upregulation by Oxidative Stress in Glioma Cells", Biochimica et Biophysica Acta, vol. 1512, pp. 335-344, 2001.
Lackman et al., "Innate Immune Recognition Triggers Secretion of Lysosomal Enzymes by Macrophages", Traffic, vol. 8, pp. 1179-1189, 2007.
Lo et al., "The xc Cystine/Glutamate Antiporter: A Mediator of Pancreatic Cancer Growth With a Role in Drug Resistance", British Journal of Cancer, vol. 99, pp. 464-472, 2008.

(Continued)

*Primary Examiner* — Michael G Hartley
*Assistant Examiner* — Sean R Donohue
(74) *Attorney, Agent, or Firm* — Eileen B. Gallagher

(57) ABSTRACT

Imaging agents are described that comprise labeled substrates capable of being introduced into cells via the cystine/glutamate antiporter. The substrates may be used for imaging or detecting oxidative stress in cells by introducing the labeled agents into cells via the cystine/glutamate antiporter and subsequent detection.

8 Claims, No Drawings

(56) References Cited

OTHER PUBLICATIONS

Mawatari et al., "Reactive Oxygen Species Involved in the Glutamate Toxicity of C6 Clioma Cells via XC Antiporter System", Neuroscience, vol. 73, No. 1, pp. 201-208, 1996.
Patel et al., "Differentiation of Substrate and Non-Substrate Inhibitors of Transport System xc: An Obligate Exchanger of L-Glutamate and L-Cystine", Neuropharmacology, vol. 46, pp. 273-284, 2004.
Plathow et al., "Tumor Cell Metabolism Imaging", The Journal of Nuclear Medicine, vol. 49, No. 6, pp. 43S-63S, Jun. 2008.
Sato et al., "Induction of Cystine Transport Activity in Mouse Peritoneal Macrophages by Bacterial Lipopolysaccharide", Biochem. Journal, vol. 310, pp. 547-551, 1995.
Sato et al., "Induction of Cystine Transport via System xc and Maintenance of Intracellular Glutahione Levels in Pancreatic Acinar and Islet Cell Lines", Biochimica et Biophysica Acta, vol. 1414, pp. 85-94, 1998.
Sato et al., "Cloning and Expression of a Plasma Membrane Cystine/Glutamate Exchange Transporter Composed of Two Distinct Proteins", The Journal of Biological Chemistry, vol. 274, No. 17, pp. 11455-11458, 1999.
Varagnolo et al., "F-Labeled Radiopharmaceuticals for PET in Oncology, Excluding FDG", Nuclear Medicine & Biology, vol. 27, pp. 103-112, 2000.
Wu et al., "Glutathione Metabolism and Its Implications for Health", downloaded from jn.nutrition.org, pp. 489-492, 2003.
Taguchi et al., "Induction of Cystine/Glutamate Transporter in Bacterial Lipopolysaccharide Induced Endotoxemia in Mice", Journal of Inflammation, vol. 4, No. 20, pp. 1-7, 2007.
Mease et al., "N-[N-[(S)-1,3-Dicarboxypropyl]Carbamoyl]-4-[18F]Fluorobenzyl-L-Cysteine, [18F]DCFBC: A New Imaging Probe for Prostate Cancer", Clin Cancer Res, vol. 14, No. 10, pp. 3036-3043, May 15, 2008.
De Bruin et al., "1[3-(2-[18F}Fluoropyridin-3-yloxy)propyl]pyrrole-2,5-dione: Design, Synthesis, and Radiosynthesis of a New [18F]Fluoropyridine-Based Maleimide Reagent for the Labeling of Peptides and Proteins", Biconjugate Chem., vol. 16, pp. 406-420, 2005.
Berndt et al., Labeling of Low-Density Lipoproteins Using the 18F-Labeled Thiol-Reactive Reagent N-[6-(4-[18F]Fluorobenzylidene)Aminooxyhexyl]Maleimide, Nuclear Medicine and Biology, vol. 34, pp. 5-15, 2007.
Poethko et al., "Chemoselective Pre-Conjugate Radiohalogenation of Unprotected Mono- and Multimeric Peptides via Oxime Formation", Radiochim. Acta, vol. 92, pp. 317-327, 2004.
Koglin et al., "Specific PET Imaging of xc Transporter Activity Using a 18F-Labeled Glutamate Derivative Reveals a Dominant Pathway in Tumor Metabolism", Clinical Cancer Research, Abstract.
Mittra et al., "Studies of the 18F L-Glutamate Derivative BAY 94-9392 in Cancer Patients; A Novel Radiopharmaceutical for PET Imaging", J. Nucl. Med, vol. 52, (Supplement 1): 1900, 2011, Abstract.
Ploessl et al., "Comparison of Cell Uptake of Fluorine-18 Labeled (2S,4R)-4-Fluoro-Glutamine (FGln) and(2S,4R)-4-Fluoro-Glutamic Acid (FGlu)", Nucl. Med, vol. 52, (Supplement 1): 1569, 2011, Abstract.
Baek et al., "First Experience With BAY 94-9392, A Novel F-18 L-Glutamate Derivative, for PET/CT Imaging in Patients With Non-Small Cell Lung and Breast Cancer", Nucl. Med, vol. 52, (Supplement 1): 195, 2011, Abstract.
Koglin et al., "BAY 94-9392—A Novel F-18 L-Glutamate Derivative for Tumor-Specific PET Imaging", Nucl. Med, vol. 52, (Supplement 1): 412, 2011, Abstract.
Smolarz et al., "BAY 94-9392: A Novel F-18 Labeled Tumor Specific Probe for PET/CT Imaging—Dosimetry", . Nucl. Med, vol. 52, (Supplement 1): 1465, 2011, Abstract.
Search Report and Written Opinion from corresponding PCT Application No. PCT/US2012/053861 dated Nov. 19, 2012.
Hijarrubia et al., "Domain structure characterization of the multifunctional [alpha]-aminoadipate reductase from Penicillium chrysogenum by limited proteolysis: Activation of [alpha]-aminoadipate does not require the peptidyl carrier protein box or the reduction domain", Journal of Biological Chemistry, vol. 278, No. 10, pp. 8250-8256, Mar. 7, 2003.
O'Sullivan et al., "Incorporation of 3H from delta-(L-alpha-amino (4,5-3)adipyl)-L-cysteinyl-D-(4,4-3H)valine into isopenicillin N.", Biochem J., vol. 182(2), pp. 421-426, 1979.

\* cited by examiner

LABELED MOLECULAR IMAGING AGENTS AND METHODS OF USE

STATEMENT REGARDING FEDERALLY SPONSORED RESEARCH AND DEVELOPMENT

This invention was made with Government support under contract number 5R01 EB014250-02 awarded by the National Institute of Health (NIH). The Government has certain rights in the invention.

BACKGROUND

The invention relates generally to labeled molecular imaging agents and more particularly to imaging agents that are taken up by the cells via the cystine/glutamate transporter.

The concept of molecular imaging promises specific contrast enhancement of molecular signatures of pathology and requires targetable biomarkers that are specifically regulated in certain pathological indications. While such a specific molecular contrast agent could have great utility for imaging and diagnosing disease; validation of a truly specific biomarker has proven to be very difficult. Even if an agent to such a specific biomarker is created, the market for such an agent will be limited to the prevalence of this indication. Therefore there is great interest in developing molecular contrast agents that can be utilized to image a variety of pathological indications. Most imaging agents target specific tissue or cell types, or specific therapies, or they degrade rapidly over time. One example of an agent that is directed at broader applications is $^{18}$F-fluorodeoxyglucose (FDG) that makes use of the glucose transporter. $^{18}$F-FDG is preferentially taken up by cells that have an increased requirement for glucose, and then is trapped inside the cell. FDG can be used clinically for the diagnosis, staging and monitoring of many cancers as well as monitoring metabolism in the heart and brain. $^{18}$F-FDG is not a substrate for sodium-dependent glucose transporters found in the kidney tubules, which prevents its renal resorption and enhances clearance In vivo oxidative stress is recognized as an indicator of cellular stress. Efforts to image this stress have involved imaging animals using electron paramagnetic resonance (EPR). EPR is a technique for detecting unpaired electrons as would occur with the creation of free radicals in oxidative stress. Essentially an agent is used which is considered to be an EPR probe which is sensitive to organ antioxidative activity as a measure of oxidative stress.

Others have looked at using a $^{13}$C-glycine chemical shift MRI to detect glycine uptake and conversion to glutathione in an animal model of chemotherapy treatment of tumors in vivo. Still others, having developed imaging agents to detect apoptotic cells in vivo for monitoring chemotherapy treatment (e.g. labeled Annexin V which is a rather large protein, Aposense by Neurosurvival Technologies which is a family of small molecules which is reported to enter specifically into only apoptotic cells.

Also reported are imaging agents that take advantage of the cellular amino acid transporter (cystine/glutamate antiporter, $x_c^-$), which is activated under conditions of cellular oxidative stress. This is described in U.S. patent application Ser. No. 12/430,573 filed on Apr. 27, 2009 and U.S. patent application Ser. No. 13/234,210 filed on Sep. 16, 2011 which are incorporated herein by reference.

It advantageous to further exploit the cystine/glutamate antiporter transport mechanism using other substrates which take advantage of the transport mechanism with other properties. For example, structures that can be readily modified using standard radiofluorination techniques are preferred as it would allow a precursor to be supplied and prepared at a point of care. Furthermore structures, which can be prepared as a single enantiomer as compared to a racemic mixture may be preferable for use as a pharmaceutical agent.

BRIEF DESCRIPTION

The imaging agents and methods of the invention take advantage of the cellular amino acid transporter (cystine/glutamate antiporter, $x_c^-$) which is activated under conditions of cellular oxidative stress. Additionally, the upregulation of the cystine/glutamate transporter is also associated with chemotherapy resistance in some tumors. Therefore, non-invasive imaging of tumors with high cystine uptake could result in identification of tumors likely to be resistant to certain therapies; which could result in efficacious changes in treatment regimens.

An embodiment of the invention, comprises an imaging agent comprising Formula I

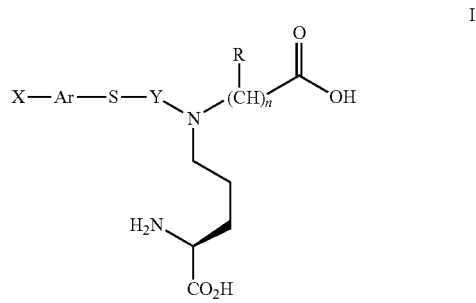

wherein R is H or $C_1$-$C_5$ alkyl;
Y is acyl or sulfonyl;
S=null, —O—$CH_2$—, —$C_2H_4$—, or —$CH_2$—O—
Ar=aryl or substituted aryl
X is $^{18}$F, $^3$H, —$(CH_2)_m$Z, or —O—$(CH_2)_m$Z;
Z is $^{18}$F or $^3$H;
n is an integer between 1 and 3; and
m is an integer between 1 and 5.

Another embodiment of the invention comprises a method of imaging cells using the imaging agent Formula I. An example of the method generally comprises introducing into the target an imaging agent comprising $^{18}$F or $^3$H labeled derivative of Formula I via the cystine/glutamate transporter; and detecting the imaging agent using one or more of, positron emission tomography (PET), autoradiography, scintillation detection, or a combination thereof.

Still another embodiment comprises a method of detecting oxidative stress in cells by introducing the $^{18}$F or $^3$H labeled derivative of Formula I via the cystine/glutamate transporter.

DETAILED DESCRIPTION

To more clearly and concisely describe and point out the subject matter of the claimed invention, the following definitions are provided for specific terms, which are used in the following description and the appended claims.

In the context of the present invention, alkyl is intended to include linear, branched, or cyclic hydrocarbon structures and combinations thereof, including lower alkyl and higher alkyl. Preferred alkyl groups are those of $C_{20}$ or below. Lower alkyl refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple bond, respectively.

Aryl and heteroaryl mean a 5- or 6-membered aromatic or heteroaromatic ring containing 0-3 heteroatoms selected from nitrogen, oxygen or sulfur; a bicyclic 9- or 10-membered aromatic or heteroaromatic ring system containing 0-3 heteroatoms selected from nitrogen, oxygen or sulfur; or a tricyclic 13- or 14-membered aromatic or heteroaromatic ring system containing 0-3 heteroatoms selected from nitrogen, oxygen or sulfur. The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl and phenethyl. Heteroarylalkyl means an alkyl residue attached to a heteroaryl ring. Examples include pyridinylmethyl and pyrimidinylethyl. Alkylaryl means an aryl residue having one or more alkyl groups attached thereto. Examples are tolyl and mesityl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle means a cycloalkyl or aryl residue in which one or two of the carbon atoms are replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted refers to residues, including, but not limited to, alkyl, alkylaryl, aryl, arylalkyl, and heteroaryl, wherein up to three H atoms of the residue are replaced with lower alkyl, substituted alkyl, alkenyl, substituted alkenyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$.

As used herein, the term "cystine/glutamate transporter" are used interchangeably with, and include, the terms cystine/glutamate antiporter, cystine/glutamate exchanger, cystine transporter, xc-, xc(-), Xc(-), system xc(-), and amino acid transport system Xc(-). The transport system comprises dimer of two proteins and includes, but is not limited to: protein xCT (SLC7A11) and protein CD98 (4F2hc, heavy chain of the 4F2 surface antigen, SLC3A2); protein xCT which is the subunit specific to the xc(-) system; protein CD98 which is a subunit common to a number of transporters with different substrates; and protein xCT that may also dimerize with rBAT, another subunit common to multiple transporters. Also the notations L-ASU and L-Asu both correspond to L-aminosuberic acid.

The cystine/glutamate transporter is not typically expressed or has extremely low expression in most tissues, but is upregulated in cells exposed to oxidative stress. Cystine, which comprises two disulfide-linked cysteine amino acids, is a natural substrate for this transporter. The effect of upregulation of the transporter is an increase in cystine uptake; which is then reduced to cysteine inside the cell. Intracellular cysteine is the rate limiting substrate for glutathione synthesis. Glutathione is the cells primary antioxidant to defend against oxidative stress. Intracellular cysteine is incorporated into one of two pathways, glutathione synthesis or protein synthesis.

As used herein, the term "radioisotopic label" includes, but is not limited to, radioisotopes that are used in a compound to trace or visualize the compound, or the mechanism of a chemical reaction, in a chemical or biological process, or biological substances, organisms and systems. Such labels are useful, for example, in connection with imaging and detection systems. Examples of suitable radioisotopic labels include, but are not limited to $^3H$, $^{123}I$, $^{125}I$, $^{131}I$, $^{18}F$, $^{11}C$, $^{62}Cu$, $^{64}Cu$, $^{67}Cu$, $^{67}Ga$ and $^{68}Ga$.

"Parenteral administration" refers to any means of introducing a substance or compound into a subject, that does not involve oral ingestion or direct introduction to the gastrointestinal tract, including but not limited to subcutaneous injection, intraperitoneal injection, intramuscular injection, intravenous injection, intrathecal injection, intracerebral injection, intracerebroventricular injection, intraspinal injection, intrathecal injection, intracerebral injection, intracerebroventricular injection, or intraspinal injection or any combination thereof.

"Pharmaceutical carrier" refers to a composition which allows the application of the agent material to the site of the application, surrounding tissues, or prepared tissue section to allow the agent to have an effective residence time for specific binding to the target or to provide a convenient manner of release. Solubilization strategies may include but are not limited to: pH adjustments, salt formation, formation of ionizable compounds, use of co-solvents, complexation, surfactants and micelles, emulsions and micro-emulsions. The pharmaceutical carrier may include, but is not limited to, a solubilizer, detergent, buffer solution, stabilizers, and preservatives. Examples of these include but are not limited to, HCl, citric acid, DMSO, propylene glycol, ethanol PEG 300, cyclodextrans, citrate, acetate, phosphate, carbonate or tris(hydroxymethyl)aminomethane.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Generally, the imaging agents of the invention comprise radioisotopic labeled analogs represented by Formula I that maintain the attributes necessary to be a substrate of the cystine/glutamate antiporter,

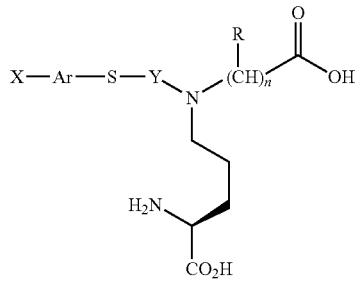

wherein R is H or $C_1$-$C_6$ alkyl;
Y is acyl or sulfonyl;
S=null, —O—$CH_2$—, —$C_2H_4$—, —$CH_2$—O—
Ar=Aryl or substituted aryl;
X is $^{18}F$, $^{3}H$, —$(CH_2)_mZ$, or —O—$(CH_2)_mZ$;
Z is $^{18}F$ or $^{3}H$;
n is an integer between 1 and 3; and
m is an integer between 1 and 5.

In certain embodiments R is hydrogen. In other embodiments R is a lower from 1 to 4 carbon atoms, and includes methyl, ethyl, n-propyl, isopropyl, and n-, s- and t-butyl. In other embodiments R is preferably methyl or ethyl. In certain embodiments n is equal to one and Y is a carbonyl group.

In certain embodiments X is —$(CH_2)_mZ$ whereby m is equal to 2 and Z is $^{18}F$. In other embodiments, X is located at the para position relative to the acyl or sulfonyl moiety.

In one embodiment Formula I is:

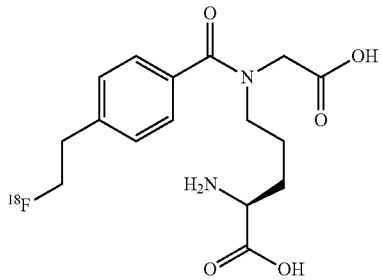 [SMILES: N[C@@H](CCCN(CC(=O)O)C(=O)c1ccc(CC[18F])cc1)C(=O)O]

In another embodiment Formula I is:

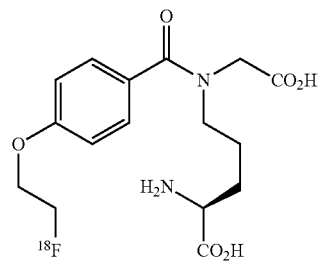 [SMILES: N[C@@H](CCCN(CC(=O)O)C(=O)c1ccc(OCC[18F])cc1)C(=O)O]

In still other embodiments Formula I is:

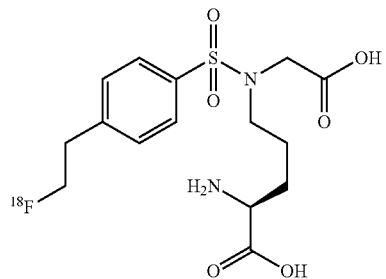 [SMILES: N[C@@H](CCCN(CC(=O)O)S(=O)(=O)c1ccc(CC[18F])cc1)C(=O)O]

In still other embodiments Formula I is:

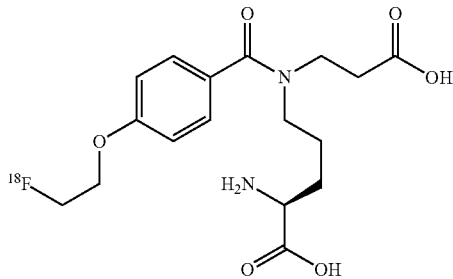 [SMILES: N[C@@H](CCCN(CCC(=O)O)C(=O)c1ccc(OCC[18F])cc1)C(=O)O]

Formula I has a single chiral center. In certain embodiments, Formula I is in the L-isomer (levo-rotatory) which is synthesized from the L-ornithine scaffold. The L-scaffold is distinctly different than other analogs in its class and has improved properties as a cystine/glutamate transporter imaging agent as shown in aforementioned U.S. application Ser. No. 13/234,210.

In certain pharmaceutical application, the development of an individual enantiomer is preferred over racemates and racemic mixtures. Such mixtures usually require specialized chiral techniques for their correct identification, characterization, separation and measurement. They are often readily distinguished by biological systems, however, and may have different pharmacokinetic properties (absorption; distribution, biotransformation. and excretion) and quantitatively or qualitatively different pharmacologic or toxicologic effects. As such when stereoisomers are biologically distinguishable, the properties of the individual enantiomers should be characterized since racemates raise issues of acceptable manufacturing control of synthesis and impurities, adequate pharmacologic and toxicologic assessment, proper characterization of metabolism and distribution, and appropriate clinical evaluation. Thus the occurrence of Formula I as an individual enantiomer is also advantageous, with a single enantiomer at the L-ornithine a carbon, and no stereoisomers at the radiofluorinated carbon primary center, unlike earlier structures with fluorine at a secondary carbon that lead to a diasteromeric mixture of fluorinated products.

The imaging agents may be detected by radioisotopic label. The method of detection of the compounds may include, but are not necessarily limited to, nuclear scintigraphy, positron emission tomography ("PET"), single photon emission computed tomography ("SPECT"), magnetic resonance imaging, magnetic resonance spectroscopy, computed tomography, or a combination thereof depending on the intended use and the imaging methodology available to the medical or research personnel.

The mechanism of cellular retention of these compounds will be by one of two mechanisms. For those compounds that are substrates for the transporter, when the labeled compounds are transported into the cell, they may not be incorporated into the protein synthesis or glutathione synthesis pathways. While it is possible that the compound could be transported out of the cell via the same transporter; the intracellular concentration of L-Glutamate is extremely high and therefore would be the favored substrate for cellular export, resulting in trapping of the majority of the compound in the cells. For those compounds that are not transporter substrates, the mechanism of cellular retention will relate to the affinity of the compound for the transport channel. These channel blockers will be retained as they physically block the transport channel and therefore will be limited to 1 to 1 stoichiometry of compound to transporter protein.

In a wide variety of human tissues and cells examined, the $x_c^-$ transporter is predominantly expressed in brain, but also in pancreas and in cultured cell lines. The $x_c^-$ transporter-expression is very low in most tissues, but can be upregulated under conditions of oxidative stress and when cells are grown in culture. The $x_c^-$ transporteris induced under a number of conditions, including apoptotic stimuli, oxidative stress, inflammation, cystine deprivation and chemotherapy resistance. For example, $^{18}F$, may be used for in vivo PET imaging, as well as in vitro detection of cellular oxidative stress.

Similarly the upregulation of the cystine/glutamate transporter is also associated with chemotherapy resistance in some tumors. Therefore, non-invasive imaging of tumors with high cystine uptake could result in identification of tumors likely to be resistant to certain therapies; which could result in efficacious changes in treatment regimens.

These agents that are taken up into cells may be used to image cellular oxidative stress in vivo, including without limitation, the imaging of pathologies or conditions that include cellular oxidative stress. Imaging applications that would benefit from these agents include, but are not limited to, chemotherapy treatment monitoring, ischemia/stroke, inflammation, traumatic brain injury and organ transplant monitoring.

The imaging agents of Formula I, can be incorporated into pharmaceutical compositions suitable for administration into a subject, which pharmaceutical compositions comprise a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible with the subject. Particularly, the carrier is suitable for intravenous, intramuscular, subcutaneous, or parenteral administration (e.g., by injection). Depending on the route of administration, the imaging agent of Formula I may be coated in a material to protect the compound or compounds from the action of acids and other natural conditions that may inactivate the compound or compounds.

In yet another embodiment, the pharmaceutical composition comprising the imaging agent of Formula I and a pharmaceutically acceptable carrier can be administered by combination therapy, i.e., combined with other agents. For example, the combination therapy can include a composition of the present invention with at least a therapeutic agent or drug, such as an anti-cancer or an antibiotic. Exemplary anti-cancer agents include cis-platin, adriamycin, and taxol. Exemplary antibiotics include isoniazid, rifamycin, and tetracycline.

In certain embodiments, the agent of Formula I is synthesized at a time sensitive or point of care location due to the decay of the material. As such, ease of manufacturing, purification, and handling are key in preparation a combination of a modular, automated, or micro-scale system is preferred. To accommodate such a need, in certain embodiments, the agent of Formula I is a single-label compound wherein a single radioisotope label is disposed as a substituent of the aryl moiety. To this end, conversion of a primary tosylate to a primary $^{18}F$ ligand is more facile than conversion at a secondary, tertiary, or aryl center, thus a final radioligand with a primary $^{18}F$ is preferred in certain embodiments.

It is understood that the position of the radioisotope label may be positioned in other locations. In certain other embodiments, the compound may be labeled at multiple locations along the alkyl chain. However for ease of manufacturing in a time sensitive or point of care locations, the radioisotope label is a single moiety as shown.

Following are non-limiting examples used to illustrate various embodiments of the imaging agents and methods of use.

Experimental Procedures:

A number of examples were synthesized according to the method described below. The non-labelled analogs final products (3a-w) are shown in Table 2 below.

General Synthesis of Intermediates 2a-r and Products 3a-r

Scheme 1:

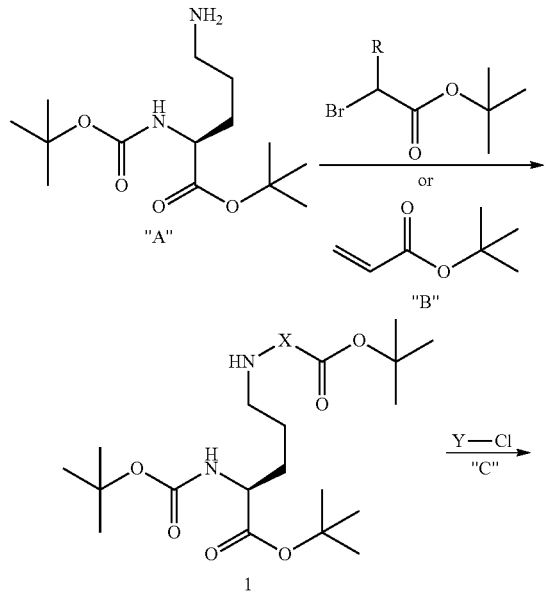

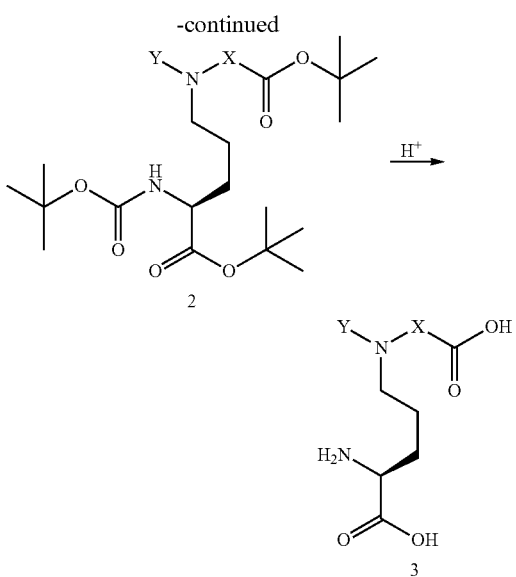

Reactant B (tert-butyl bromoacetate, 74 uL, 500 umole, or tert-butyl acrylate, 73 uL, 500 umole) was added to a vial containing Reactant A, 162 mg of Boc-Orn-OtBu HCl (500 umole, 324.85 g/m) or 169 mg of Boc-Lys-OtBu HCl (500 umole, 338.85 g/m) and 200 uL of triethylamine in 2 ml of methylene chloride. The vials were capped and shaken for 16 hours. 100 umole of Reactant C (substituted acid chloride, sulfonyl chloride, or chloroformate) was then added, and the mixtures shaken for an additional 2 hours. 1 ml of water was added to each, and the mixtures were shaken for 10 minutes. The layers were separated, and the aqueous layers were washed twice with 1 ml portions of methylene chloride. The combined organic layers were stripped, and the residues were chromatographed on 4 gm silica gel columns with hexane/ethyl acetate as eluent. Intermediates 2a-r were characterized by LCMS, with structures confirmed by positive ion mass spectrometry.

The BOC, t-butyl ester protected intermediates 2a-r were each dissolved in 1 ml of methylene chloride, and 1 ml of trifluoroacetic acid was added. The mixtures were stirred at room temperature for 14 hours, after which time the volatiles were removed from each under reduced pressure. The residues were dissolved in 2 ml of water and lyophilized for 24 hours, yielding the TFA salts. The final products 3a-r were characterized by LCMS, both positive and negative ion.

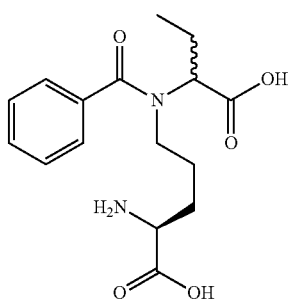

Tert-butyl 2-bromobutanoate (111 mg, 500 umole)) was added to a vial containing 162 mg of BOC-Orn-OtBu HCl (500 umole, 324.85 g/m) and 200 uL of triethylamine in 2 ml of acetonitrile. The vial was capped and shaken for 16 hours. 100 umole of benzoyl chloride was then added, and the mixture shaken 16 hours at 50° C. The mixture was then cooled, the volatiles were removed under reduced pressure, and the residue was partitioned between 1 ml of methylene chloride and 1 ml of water. The layers were separated, and the aqueous layer was washed twice with 1 ml portions of methylene chloride. The combined organic layers were stripped, and the residue was chromatographed on a 4 gm silica gel column with hexane/ethyl acetate as eluent, and product 2w characterized by LCMS, with structure confirmed by positive ion mass spectrometry. The material was deprotected using 1:1 methylene chloride and trifluoroacetic acid using the same method described in the general library synthesis, yielding product 3w, characterized by LCMS with structure confirmed by positive and negative ion mass spectrometry.

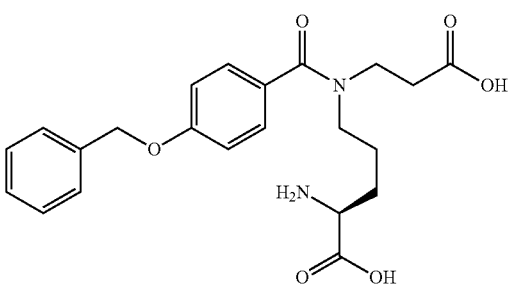

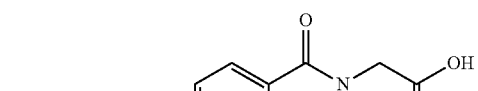

225 ul of reactant B (tert-butyl 2-bromoacetate, 3000 umole or tert-butyl acrylate, 3000 umole) was added to a vial containing 500 mg of BOC-Orn-OtBu HCl (3000 umole, 324.85 g/m) and 400 uL of triethylamine in 5 ml of methylene chloride. The vials were capped and shaken for 16 hours. 500 mg of 4-benzyloxybenzoyl chloride along with 1.0 ml of additional triethylamine and 2.0 ml of methylene chloride was then added to each, and the mixtures shaken 2 hours at 25° C. 5 ml of water was then added to each, the layers were separated, and the aqueous layer was washed twice with 5 ml portions of methylene chloride. The combined organic layers were stripped, and the residue was chromatographed on a 4 gm silica gel column with hexane/ethyl acetate as eluent. Intermediates 2u and 2v were characterized by LCMS, with structure confirmed by positive ion mass spectrometry. 20 mg of each was deprotected using 1:1 methylene chloride and trifluoroacetic acid using the same method described in the general library synthesis, yielding products 3u and 3v, characterized by LCMS with structure confirmed by positive and negative ion mass spectrometry.

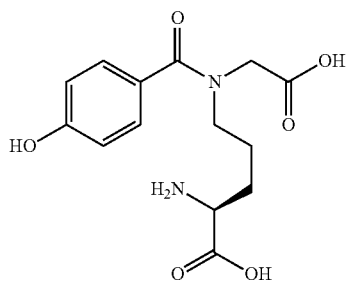

3s

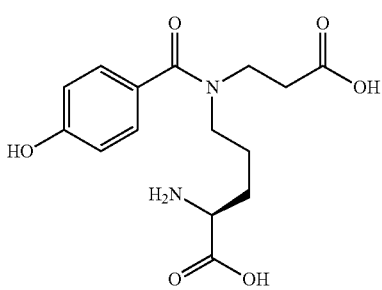

3t 200 mg each of protected intermediates 2u and 2v in 5 ml EtOH were hydrogenated overnight with 20 mg of 10% palladium on carbon catalyst. The catalyst was then filtered off, and the solvent was removed under reduced pressure, yielding the protected derivative of structure 2s and 2t. The product was characterized by LCMS, and 20 mg of each was deprotected with 1:1 trifluoroacetic acid and methylene chloride using the same method described in the general library synthesis, yielding product 3s and 3t, characterized by LCMS, with structure confirmed by positive and negative ion mass spectrometry.

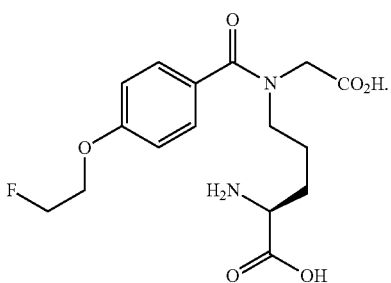

3x 604 mg (4.0 mmol) of methyl 4-hydroxybenzoate, 3.26 g (26 mmol) 1-bromo-2-fluoroethane, and 3.56 g (26 mmol) of potassium carbonate were refluxed in 50 ml of acetone for 16 hours. The mixture was then cooled, and the colvent removed under reduced pressure. The residue was then dissolved in a mixture of 50 ml of ethyl acetate and 50 ml of 50% saturated sodium bicarbonate solution. The layers were separated, and the solvent was removed from the organic layer under reduced pressure. The residue was then chromatagraphed with hexane/ethyl acetate as eluent, yielding 762 mg of methyl-4-(2-fluoroethoxyl)benzoate. This was dissolved in a mixture of 400 mg of lithium hydroxide monohydrate in 50 ml of 4:1 methanol/water, and stirred for 12 hours. The mixture was then acidified to <pH 3.0 with 6M HCl, the methanol was removed under reduced pressure, and the residue was extracted with ethyl acetate. After removing the solvent under reduced pressure, the residue was chromatagraphed on silica gel with hexane/ethyl acetate as mobile phase, yielding 620 mg of 4-(2-fluoroethoxyl) benzoic acid. In a separate vial, 200 mg (614 mmol) of Boc-Orn-OtBu HCl was dissolved in 2 ml of dimethylformamide with 160 uL of triethylamine. 90 uL (614 mmol) of tert-butylbromoacetate was then added, and the mixture was stirred for 16 hours. In a separate flask, 226 mg (1.228 mmol) of 4-(2-fluoroethoxyl)benzoic acid was added to a mixture of 377 mg (2.456 mmol) 1-chloro-N,N,2-trimethylprop-1-ene-1-amine in 4 ml of dimethylformamide. The mixture was stirred for 2 hours, then added to the solution of the ornithine derivative from above, and stirred an additional 2 hours. 5 ml of 2:1 toluene/ethyl acetate and 10 ml of water were then added, the organic layer was separated, and the aqueous layer was extracted twice more with equal quantities of toluene/ethyl acetate. The solvent from the combined organic layers was removed under reduced pressure, and the residue was chromatographed on silica gel with hexane/ethyl acetate as eluent, yielding 76 mg of 2x. 11 mg of this material was dissolved in 1 ml of cold methylene chloride, and 1 ml of trifluoroacetic acid was added. The mixture was stirred for 16 hours at room temperature, at which time the solvents were removed under reduced pressure. The residue was dissolved in 2 ml of water and lyophilized, yielding 6 mg of 3x.

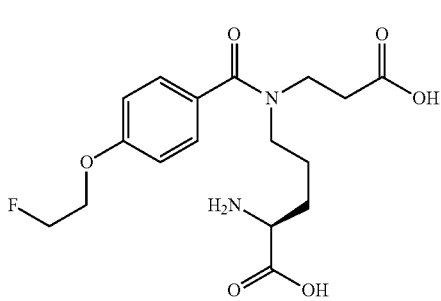

3y 200 mg (614 mmol) of Boc-Orn-OtBu HCl was dissolved in 2 ml of dimethylformamide with 160 uL of triethylamine. 90 uL (614 mmol) of t-butyl acrylate was then added, and the mixture was stirred for 16 hours. In a separate flask, 226 mg (1.228 mmol) of 4-(2-fluoroethoxyl)benzoic acid was added to a mixture of 377 mg (2.456 mmol) 1-chloro-N,N, 2-trimethylprop-1-ene-1-amine in 4 ml of dimethylformamide. The mixture was stirred for 2 hours, then added to the solution of the ornithine derivative, and stirred an additional 2 hours. 5 ml of 2:1 toluene/ethyl acetate and 10 ml of water were then added, the organic layer was separated, and the aqueous layer was extracted twice more with equal quantities of toluene/ethyl acetate. The solvent from the combined organic layers was removed under reduced pressure, and the residue was chromatographed on silica gel with hexane/ ethyl acetate as eluent, yielding 160 mg of 2y. 30 mg of this material was dissolved in 1 ml of cold methylene chloride, and 1 ml of trifluoroacetic acid was added. The mixture was stirred for 16 hours at room temperature, at which time the solvents were removed under reduced pressure. The residue was dissolved in 2 ml of water and lyophilized, yielding 22 mg of 3y.

Tosylated Precursor

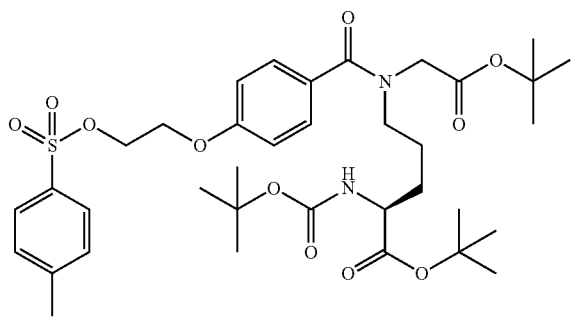 [SMILES: Cc1ccc(S(=O)(=O)OCCOc2ccc(C(=O)N(CCC[C@H](NC(=O)OC(C)(C)C)C(=O)OC(C)(C)C)CC(=O)OC(C)(C)C)cc2)cc1]

4-(2-hydroxyethoxyl)benzoic acid (424 mg, 2.33 mmol) and 1.3 ml of triethylamine were dissolved in 10 ml of methylene chloride Four equivalents of acetic anhydride were added, and the mixture was stirred for 16 hours at room temperature. The solvents and excess triethyl amine was then removed by rotary evaporation, and the residue was partitioned between 5 ml each of methylene chloride and water. The 2-phase mixture was acidified to pH 2.0, the layers were separated, and the aqueous layer was extracted twice with 5 ml portions of methylene chloride. The solvent was removed under reduced pressure from the combined organic layers, and the product used as is for the next step.

45 uL, 308 umole of tert-butyl bromoacetate was added to a vial containing 100 mg of BOC-Orn-OtBu HCl (308 umole) and 200 uL of triethylamine in 2 ml of methylene chloride. The vial was capped and shaken for 16 hours, then the solvent and excess triethyl amine were evaporated, and the residue dissolved in 1 ml of anhydrous dimethylformamide. In a separate flask, 69 mg (308 umol) of 2-(acetoxyethoxy)benzoic acid was dissolved in 1 ml of anhydrous DMF, 82 mg (614 umol) of 1-chloro-N,N,2-trimethylprop-1-ene-1-amine was added, and the mixture stirred for 30 minutes. The DMF solution of the ornithine derivative was then added, and the mixture was stirred for 2 hours. The reaction was then quenched with 1 ml of saturated sodium bicarbonate followed by 5 ml of water. The mixture was then extracted 3× with 5 ml portions of a 1:1 mixture of ethyl acetate and hexane. The solvent was removed from the combined organic layers, and the residue was chromatagraphed on a 4 g silica gel column with hexane/ethyl acetate. The chromatographed product contained about 50% residual DMF.

The acetate product from above was dissolved in 5 ml of methanol, 90 mg of solid potassium carbonate was added, and the mixture was stirred for 6 hr. Water (2 ml) was added, and the mixture was acidified to pH 3.0 with 1N HCl. The aqueous solution was then decanted from the waxy product stuck to the sides of the flask. The residue was then chromatagraphed on a 4 g silica column with hexane/ethyl acetate, yielding 24 mg of final product.

The alcohol from above (24 mg, 42 umoles) was dissolved in 2 ml of methylene chloride with 17 mg of triethylamine, and 16 mg (84 umole) of p-toluene sulfonyl chloride was added. The mixture was stirred for 16 hours, the solvent and voltiles were removed under reduced pressure, and the residue was chromatographed on a 4 g silica column with hexane/ethyl acetate, yielding 22 mg of final product. Radioisotope labels such as $^3$H and $^{18}$F, may be particularly useful for in vivo PET as well as in vitro detection of cellular oxidative stress. While only certain features of the invention have been illustrated and described herein, many modifications and changes will occur to those skilled in the art. It is, therefore, to be understood that the appended claims are intended to cover all such modifications and changes as fall within the true spirit of the invention.

Synthesis of $^{18}$F agent may be accomplished using standard practices for radiolabelling of materials. For example: a specific, non-limiting example of the method for synthesizing a similar analog, monoAO-[$^{18}$F]-FBA-Cystine is provided as follows.

All reactions were performed either under a nitrogen atmosphere or in a crimp-top sealed vial purged with nitrogen. Kryptofix 222 (Aldrich) and K2CO3 (EMD Science) were purchased and used as received. Optima™-grade acetonitrile was used as both HPLC and reaction solvents.

[$^{18}$F]KF (40 mCi·mL-1 (1480 MBq·mL-1) in purified water) was obtained from either IBA Molecular (Albany, N.Y.) or PETNET Solutions (Albany, N.Y.) and used as received. The [$^{18}$F]fluoride was first immobilized on a Chromafix 30-PS-HCO$_3$ anion exchange cartridge (ABX, Radeberg, Germany), then eluted into a drydown vessel with a 1 mL, 4:1 mixture of acetonitrile:distilled deionized water (ddH$_2$O) containing Kryptofix K222 (376 g·mol-1, 8 mg, $2.13 \times 10^{-5}$ mol) and potassium carbonate (138.2 g·mol-1, 2.1 mg, $1.52 \times 10^{-5}$ mol). The solvent was removed under partial vacuum and a flow of nitrogen with gentle heating (~45° C.) (~15 min). The source vial and anion exchange cartridge were then washed with 0.5 mL of acetonitrile containing K222 (8 mg) and the reaction mixture again brought to dryness under partial vacuum and gentle heating (~10 min). The reaction vessel was repressurized with nitrogen and the azeotropic drydown repeated twice with an additional 0.5 mL of acetonitrile. 4-formyl-N,N,N-trimethylanilinium triflate (313.30 g·mol-1, 3.1 mg, $9.89 \times 10^{-6}$ mol) was dissolved in 0.35 mL of anhydrous DMSO (Acros) and added directly to the reaction vessel containing the [18F]KF.K222, K$_2$CO$_3$. The reaction mixture was heated to 90° C. for 15 min and immediately cooled and quenched with 3 mL of distilled, deionized H$_2$O (ddH$_2$O). This mixture was subsequently passed through a cation exchange cartridge (Waters SepPak Light Accell Plus CM), diluted to 10 mL with ddH$_2$O, and loaded onto a reverse phase C18 SepPak (Waters SepPak Plus C18). The SepPak was flushed with 10 mL of ddH$_2$O then purged with 30 mL of air. [$^{18}$F]4-fluorobenzaldehyde ([$^{18}$F]FBA), was eluted in 1.0 mL of methanol.

Separately, a high recovery vial (2 mL, National Scientific) was charged with mono-aminoxy cystine (386.27 g·mol$^{-1}$, 2.7 mg, $6.99 \times 10^{-6}$ mol). The solid was suspended in 250 µL of ddH$_2$O and 8 µL of trifluoroacetic acid. 500 µL of [18F]FBA in methanol (see above) was transferred to the reaction vial. The vessel was capped, crimped, placed in a heating block (activity at start of reaction 4.66 mCi/172 MBq) and maintained at 60° C. for 15 minutes; at which point a small aliquot (<5 µL) was removed for analytical HPLC analysis. 250 µL of ddH$_2$O with 0.1% TFA was used to dilute the solution to approx. 1000 µL, giving a final composition of 1:1 ddH$_2$O:MeOH in preparation for semi-preparative HPLC purification. [$^{18}$F]FB-Cystine was isolated and purified by semi-preparative HPLC. The HPLC fraction containing the product (0.409 mCi/15.1 MBq) was diluted 5:1 with ddH$_2$O and subsequently immobilized on a tC18 Plus Sep Pak (Waters). The SepPak was flushed first with 5 mL of ddH$_2$O then 30 mL of air. [$^{18}$F]FB-Cys (0.17 mCi, 6.3 MBq) was isolated in a minimal amount of DMSO by first eluting the void volume (approx. 0.5 mL) followed by collecting 250 to 300 µL of eluent in a separate flask. RP-HPLC analysis was performed on the isolated product in order to establish radiochemical and chemical purity. Typically, 10 μL, of a 0.1 μCi/μL solution was injected for post formulation analysis. Isolated radiochemical yield was 3.6% (6.6% decay corrected from addition of [$^{18}$F]FBA) and radiochemical purity of 96.8%.

Synthesis of $^3$H agent may be accomplished using standard practices for radiolabelling of materials. For example $^3$H may be incorporated using a catalytic reduction with $^3$H gas or introduced via reduction with isotopic hydride reagents or a transition metal-mediated exchange.

Table 1 provides examples of the non-labelled analog of the final product. Also provided are measurements of inhibition response of $^3$H-L-GLU (control) uptake in DEM treated EL4 cells. As such 96 well plate were seeded with 100,000 SKOV3 cells/well in complete growth media (Mc-Coy's+10% Fetal Bovine Serum(FBS)) and incubated overnight at 37° C. The media was changed to 100 μM DEM and again incubated overnight at 37° C. Wash 1× with Hank's Balanced Salt Solution (HBSS) Room Temperature and assayed 50 nl of each agent (Table 2) in triplicate by incubating for 30 minutes (uptake) at room temperature. It was then washed twice with HBSS and 200 μl MicroScint20 added for counting. The protocol used 200 μCi $^3$H-Glu per well. The mix and agent and $^3$H-Glu provided a final concentration of 200 μCi and 1 mM agent. The % of control, measured three times with standard deviation, shows uptake of $^3$H-Glu. As such lower response is indicative of inhibition of the transporter. As such numbers below approximately 30% is equivalent to 70% inhibition and are considered good candidates for pharmaceutical agents.

TABLE 1 non-radioactive agents and measurements of $^3$H-Glu uptake.

| Structure # | Structure 3 | % of control $^3$H-Glu uptake | standard deviation |
|---|---|---|---|
| a | 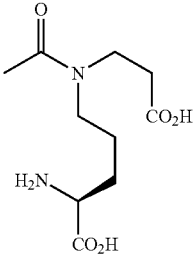 [SMILES: CC(=O)N(CCC[C@H](N)C(=O)O)CCC(=O)O] | 118.468 | 3.759 |
| b | 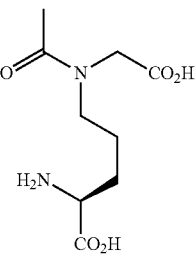 [SMILES: CC(=O)N(CCC[C@H](N)C(=O)O)CC(=O)O] | 95.742 | 1.013 |
| c | 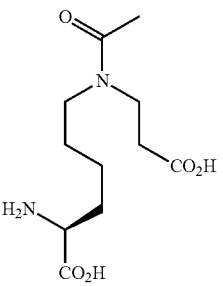 | 102.092 | 1.674 |

TABLE 1-continued
non-radioactive agents and measurements of $^3$H-Glu uptake.
| Structure # | Structure 3 | % of control $^3$H-Glu uptake | standard deviation |
|---|---|---|---|
| d | 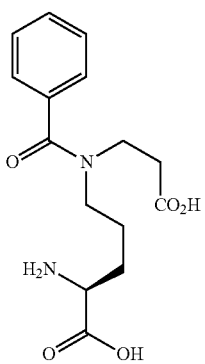 [SMILES: N[C@@H](CCCN(CCC(=O)O)C(=O)c1ccccc1)C(=O)O] | 35.978 | 1.429 |
| e | 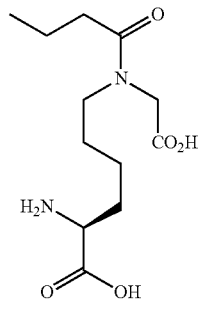 [SMILES: CCCC(=O)N(CCCC[C@H](N)C(=O)O)CC(=O)O] | 102.039 | 2.651 |
| f | 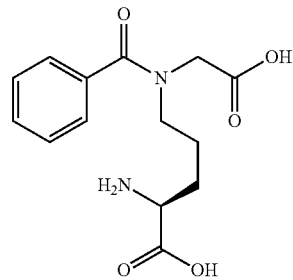 [SMILES: N[C@@H](CCCN(CC(=O)O)C(=O)c1ccccc1)C(=O)O] | 37.186 | 2.444 |
| g | 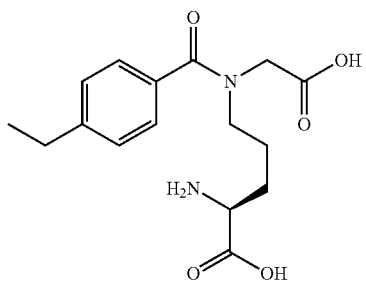 [SMILES: CCc1ccc(C(=O)N(CCC[C@H](N)C(=O)O)CC(=O)O)cc1] | 11.202 | 1.473 |
| h | 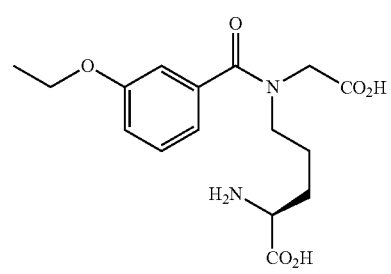 [SMILES: CCOc1cccc(C(=O)N(CCC[C@H](N)C(=O)O)CC(=O)O)c1] | 39.834 | 2.758 |

TABLE 1-continued non-radioactive agents and measurements of $^3$H-Glu uptake.

| Structure # | Structure 3 | % of control $^3$H-Glu uptake | standard deviation |
|---|---|---|---|
| i | *(structure)* | 17.299 | 2.389 |
| j | *(structure)* | 43.273 | 1.870 |
| k | *(structure)* | 11.592 | 0.847 |
| l | *(structure)* | 54.174 | 5.914 |
| n | *(structure)* | 12.283 | 5.240 |

TABLE 1-continued non-radioactive agents and measurements of $^3$H-Glu uptake.

| Structure # | Structure 3 | % of control $^3$H-Glu uptake | standard deviation |
|---|---|---|---|
| p | [structure: 1-naphthoyl-N(CH2COOH)-lysine derivative] | 12.403 | 4.392 |
| q | [structure: tosyl-N(CH2COOH)-lysine derivative] | 13.441 | 1.315 |
| r | [structure: Cbz-N(CH2COOH)-lysine derivative] | 16.402 | 11.395 |
| s | [structure: 4-hydroxybenzoyl-N(CH2COOH)-lysine derivative] | 22.411 | 2.426 |
| t | [structure: 4-hydroxybenzoyl-N(CH2CH2COOH)-lysine derivative] | 45.410 | 3.530 |

TABLE 1-continued non-radioactive agents and measurements of $^3$H-Glu uptake.

| Structure # | Structure 3 | % of control $^3$H-Glu uptake | standard deviation |
|---|---|---|---|
| u | [structure] | 12.696 | 1.182 |
| v | [structure] | not measured | |
| w | [structure] | 26.142 | 4.726 |
| x | [structure] | 13.339 | |
| y | [structure] | 10.627 | |

The invention claimed is:

1. An imaging agent comprising a compound of Formula I

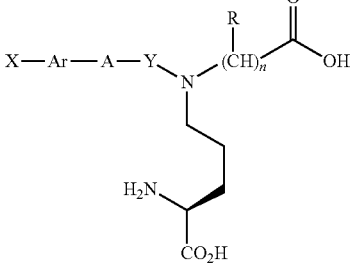

wherein R is H or $C_1$-$C_5$ alkyl;
Y is acyl or sulfonyl;
A=null, —O—$CH_2$—, —$C_2H_4$—, or —$CH_2$—O—
Ar=4-substituted phenyl, a 4-substituted naphthalene-1-yl, a 5-substituted naphthalene-1-yl, or a 6-substituted naphthalene-1-yl;
X is $^{18}F$, $^3H$, —$(CH_2)_mZ$, or —O—$(CH_2)_mZ$,
Z is $^{18}F$ or $^3H$;
n is an integer between 1 and 3; and
m is an integer between 1 and 5.

2. The agent of claim 1 wherein Y is acyl.
3. The agent of claim 2 wherein Z is $^{18}F$ or $^3H$.
4. The agent of claim 3 wherein Z is a singularly occurring $^{18}F$.
5. The agent of claim 1 wherein Formula I is

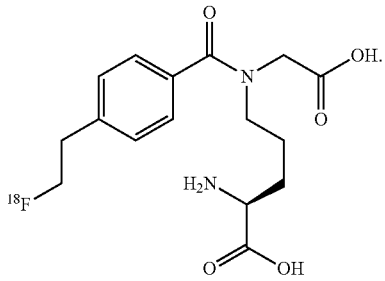 [SMILES: N[C@@H](CCCN(CC(=O)O)C(=O)c1ccc(CC[18F])cc1)C(=O)O]

6. The agent of claim 1 wherein Formula I is

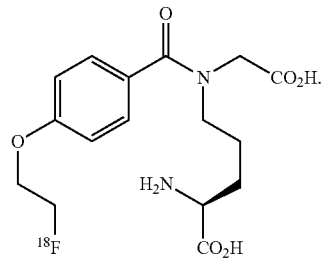 [SMILES: N[C@@H](CCCN(CC(=O)O)C(=O)c1ccc(OCC[18F])cc1)C(=O)O]

7. The agent of claim 1 wherein Formula I is

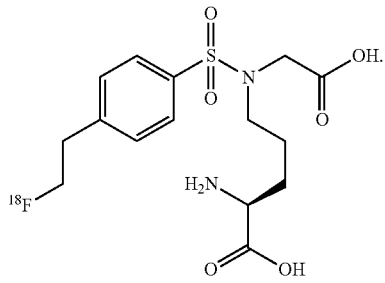 [SMILES: N[C@@H](CCCN(CC(=O)O)S(=O)(=O)c1ccc(CC[18F])cc1)C(=O)O]

8. The agent of claim 1 wherein Formula I is

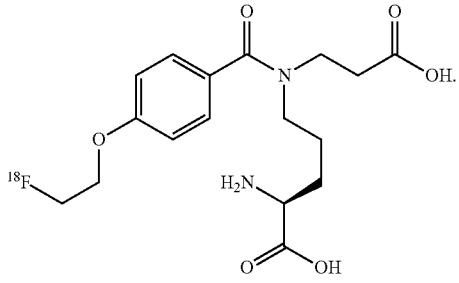 [SMILES: N[C@@H](CCCN(CCC(=O)O)C(=O)c1ccc(OCC[18F])cc1)C(=O)O]

* * * * *